United States Patent [19]

Burkhardt et al.

[11] Patent Number: 4,936,313
[45] Date of Patent: Jun. 26, 1990

[54] POWER TOOL FOR EXCISING A BONE OR CARTILAGE BIOPSY

[75] Inventors: Rolf Burkhardt, Munich, Fed. Rep. of Germany; Raymund A. Meier, Liedertswil, Switzerland

[73] Assignee: Institut Strauman AG, Waldenburg, Switzerland

[21] Appl. No.: 273,406

[22] Filed: Nov. 18, 1988

[30] Foreign Application Priority Data

Nov. 18, 1987 [CH] Switzerland ................ 4484/87

[51] Int. Cl.$^5$ .............................................. A61B 10/00
[52] U.S. Cl. .................................... 128/751; 128/754; 128/755; 606/180
[58] Field of Search ............... 128/749, 751, 754, 755, 128/305, 310; 30/278, 280, 500; 408/204, 207, 67, 68; 606/167, 170, 179, 180

[56] References Cited

U.S. PATENT DOCUMENTS 2,484,150 10/1949 Brown ................................ 408/204

4,785,826 11/1988 Ward ................................ 128/754

FOREIGN PATENT DOCUMENTS 2177307 1/1987 United Kingdom ............ 128/754

Primary Examiner—Randall L. Green
Assistant Examiner—Randy Shay
Attorney, Agent, or Firm—Toren, McGeady & Associates

[57] ABSTRACT

The tubular milling cutter adapted for excising a stud from a bone or cartilage as biopsy is screw-connected with the drive shaft of a drive mechanism. A grip chuck serving as extracting device is provided inside the tubular milling cutter. This grip chuck is adapted to be displaced forward and backward by means of a nut screw-connected with the holder for the milling cutter, whereby the opening of the grip chuck decreases during forward displacement so as to fixedly hold the stud. An ejector connected by means of a transverse pin with an ejector sleeve serving for actuation, is displaceably supported inside said grip chuck.

5 Claims, 2 Drawing Sheets

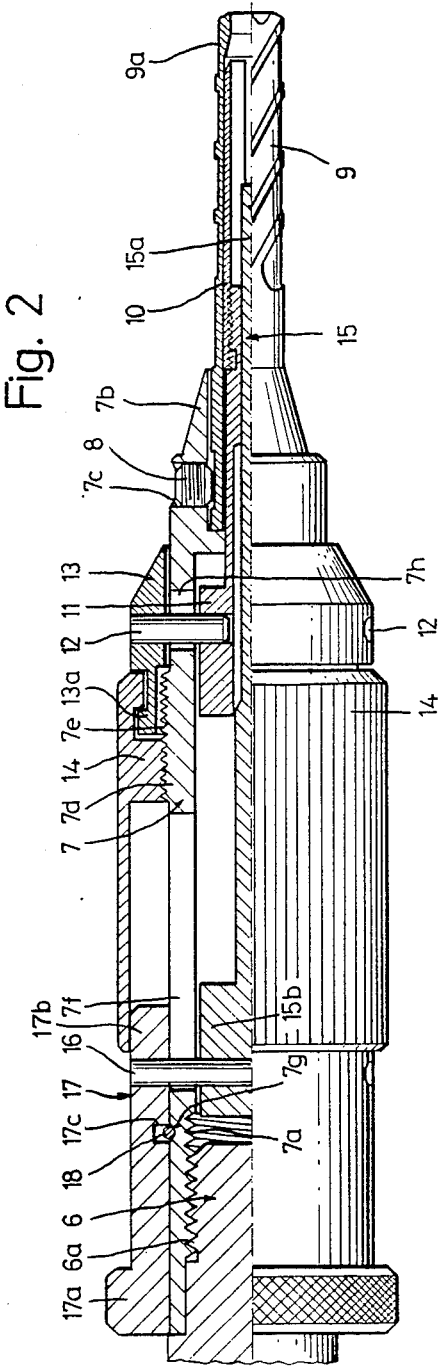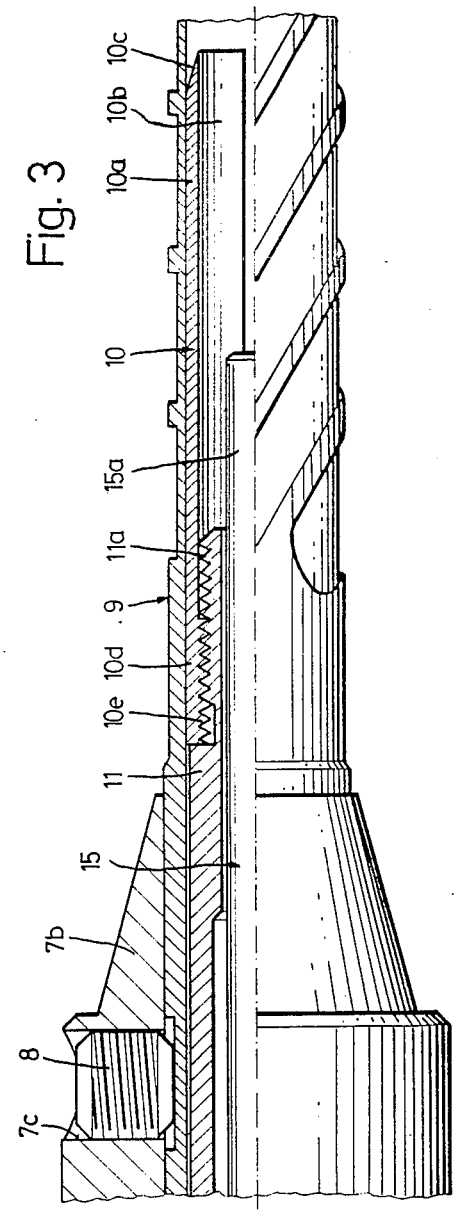

POWER TOOL FOR EXCISING A BONE OR CARTILAGE BIOPSY

BACKGROUND OF THE INVENTION

1. Field of the Invention

The present invention refers to a device for excising a bone or cartilage biopsy shaped as a stud, the device comprising a tubular a coring cutter or trephine adapted to be connected to a drive shaft of a power tool in a manner to transmit torque. In operation the tubular coring cutter is advanced into the bone or cartilage and made to bore a tubular hold and to form, during its forward movement, a cylindrical stud of a desired length in the tubular hole, the stud being broken off at its root at the end of the boring operation. Biopsies of this kind are excised in medicine for diagnostic purposes, e.g. for diagnosing cancer, biochemical, or structural ailments in bone or cartilage. The term bone will be used in the following to mean bone or cartilage, unless otherwise specified.

2. Description of the Prior Art

The excision of a biopsy of the aforementioned kind is normally performed in several steps using several instruments. First, a tubular cavity is bored into the bone by means of a power-driven tubular coring cutter. The cylindrical stud produced in the process is broken off at the base of the stud and removed from the bone by means of pliers or tweezers. This latter step is clearly far from optimum and requires special care in handling, with possible discomfort to both the doctor and the patient and even an extension of the duration of the operation. Yet, the operation is still performed in this manner for lack of other known devices that would allow simpler operation.

SUMMARY OF THE INVENTION

Hence from what has been said heretofore it should be apparent that the art is still in need of a device for excising a biopsy, which is not associated with the aforementioned drawbacks and limitations of the state-of-the-art proposals.

It is therefore a primary object of the present invention to provide a novel device for excising a biopsy, which is not associated with the drawbacks and limitations of the prior art as heretofore discussed and which effectively and reliably fulfills an existing need in the art.

Another and more specific object of the invention relates to a new and improved device for excising a biopsy that allows for more control in the manipulation of the cylindrical stud and easier removal thereof from the bone at the end of the boring operation, while providing more comfort to the doctor and the patient.

A further object of the invention relates to a new and improved device for excising a biopsy, in which the improved mechanism for handling the biopsy is effective to shorten the length of duration of the excising operation.

The foregoing and other objects are attained in accordance with one aspect of the invention by providing a device of the aforedescribed type equipped with a tubular coring cutter of trephine adapted to be connected to a drive shaft of the drilling tool in a manner to transmit torque, the device being provided with a grip chuck disposed longitudinally displaceably inside the coring cutter and serving as extractor, and an ejector is disposed longitudinally displaceably inside the grip chuck.

The invention possesses several advantages as compared to similar tools known in the art. The stud made to shape by the tubular coring cutter but still fastened at its root to the bone, may be gripped by means of the grip chuck, it may be broken off readily from the bone and immediately removed. No pliers or tweezers are needed, nor is the doctor put under undue stress by any complicated manipulations. The ejection of the stud from the grip chuck is equally uncomplicated. Thus, a more comfortable operation of reduced time duration is the net result.

Some preferred features of specific embodiments are described in the following.

The tubular coring cutter is loosenably held inside a sleeve-like coring cutter holder rigidly connected with said drive shaft. A knurled nut is displaceably disposed on said coring cutter holder and is operatively connected with a sliding sleeve. In turn, the sliding sleeve is rigidly connected by way of the grip chuck holder with a grip chuck, by means of one or more radial pins longitudinally displaceable between two end positions, within a slot of the coring cutter holder.

The grip chuck is fitted inside the bore of the tubular coring cutter, while the wall of the latter is thickened inwardly in the region of the free end of the coring cutter. The inside diameter of the coring cutter as measured at its mouth is substantially equal to the effective inside diameter of the grip chuck in its retracted position, while during forward displacement the free ends of the grip chuck are pushed closer to each other, thus effecting a decrease in the size of the grip chuck opening.

The ejector provided inside the grip chuck is preferably implemented as an axially displaceable pin fixedly connected with an ejector sleeve by means of a radially extending pin displaceable within a longitudinal slot of the coring cutter holder, between two end positions. The ejector sleeve, in turn, has its end facing away from the coring cutter fitted on the coring cutter holder and is held fast in its retracted position within a spring detent.

BRIEF DESCRIPTION OF THE DRAWINGS

The subject matter of the invention will now be explained by making reference to the appended drawing illustrating preferred embodiments of the invention. There show.

DETAILED DESCRIPTION OF THE PREFERRED EMBODIMENT

Figure 1:
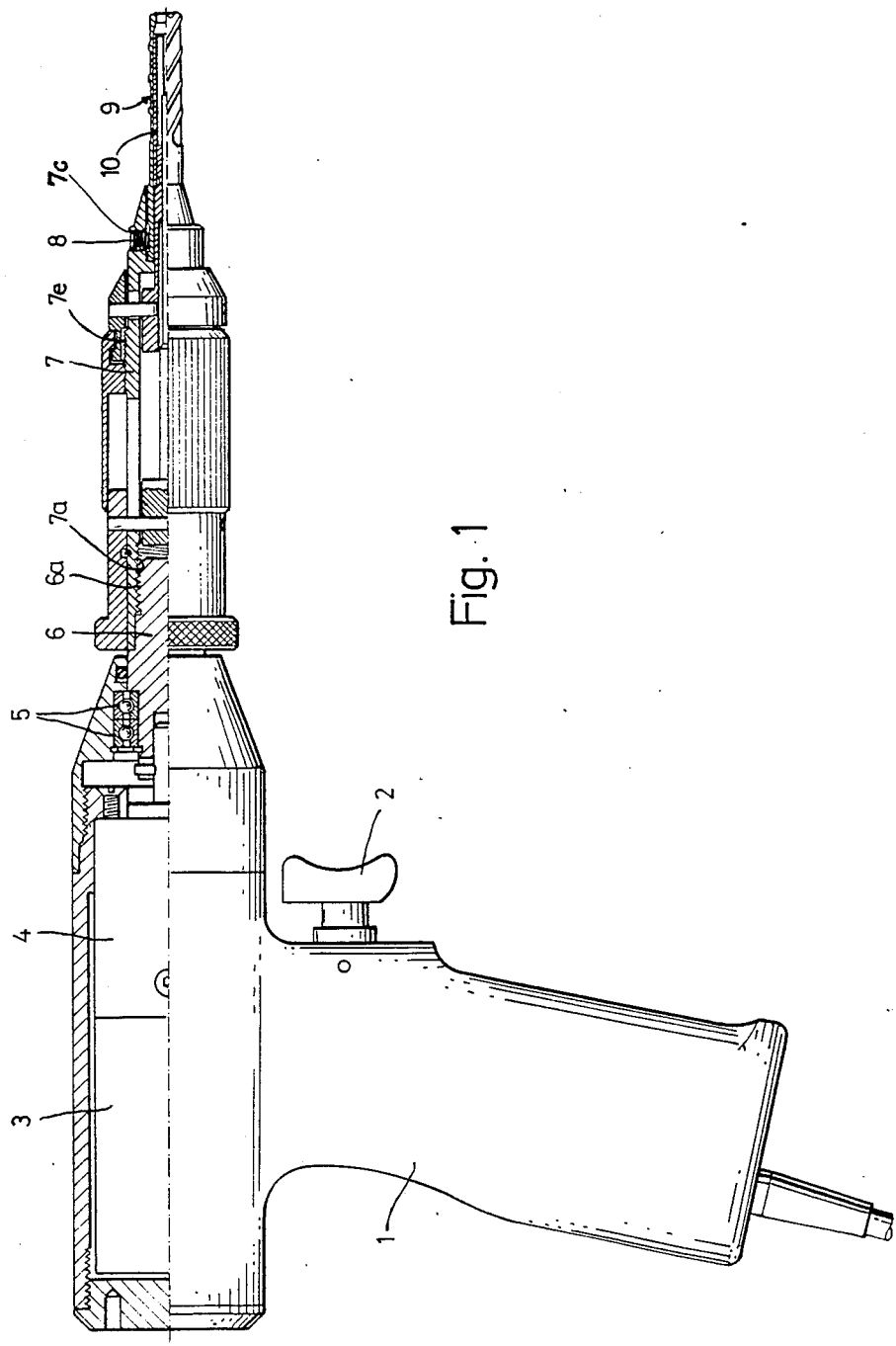
FIG. 1 an embodiment of the device complete with electrical drive shown in longitudinal plan view partially sectioned, FIG. 2 a cutaway portion of FIG. 1 shown at a larger scale, and FIG. 3 a cutaway portion of FIG. 2 shown at a larger scale.

The left half of the device illustrated in FIG. 1 corresponds to a customary electrical boring or drilling tool. It comprises a handle 1, an electrical motor 3 that may be switched on and off by means of a depressor knob 2, a speed-reducing drive 4, and a drive shaft 6 supported in ball bearings. A tubular coring cutter holder 7 comprising an internal thread 7a is screwed onto the outer thread 6a provided at the free end of the drive shaft 6, said holder 7 being provided with a conical taper 7b at its end facing away from the threaded connection. A radially extending threaded hole 7c is provided behind the conical taper 7b. In this hole 7c a socket head cap screw 8 is screwed and is adapted to loosenably hold fast the tubular coring cutter 9 inserted into the coring cutter holder and arranged to cut in clockwise direction, the screw 8 being provided with a depression, by way of which the screw 8 may be engaged by a screwdriver. This tubular coring cutter 9 differs from other tubular coring cutters used for excising biopsies only by the fact, that its wall comprises a section slightly thickened radially inwardly in the region of the free end 9a of the coring cutter. As particularly clearly shown in FIGS. 2 and 3, a grip chuck 10 is fittingly disposed inside the tubular coring cutter 9 and is subdivided to advantage at its free end 10a by three longitudinal slots, to form three ribs 10b, each rib being provided with a beveled or chamfered portion 10c at its free end. At its rear end the grip chuck 10 comprises a sleeve 10d comprising an internal thread 10e screwed onto an outer thread 11a of grip chuck holder 11. This grip chuck holder 11 is fixedly connected to a sliding sleeve 13 by way of two radially extending pins 12, the sliding sleeve 13 being disposed on the periphery of the coring cutter holder 7. In this arrangement the two slots 7h have the function of limiting, at both ends, the axial displacement of the grip chuck holder, the pins, and the sliding sleeve. This displacement is controlled in such a way, that in its front end position the grip chuck opening is closed by the thickened section 9a of the coring cutter 9, whereas in its rear position the grip chuck opening is opened, to have the grip chuck outer diameter correspond to the inside diameter of the coring cutter bore.

If a tubular coring cutter of different length is inserted into the power tool, an operation readily performed by loosening the cap screw 8, then a different grip chuck of a length adjusted to the length of the new coring cutter must be screwed onto the grip chuck holder.

The coring cutter holder 7 has a thickened portion 7d disposed behind the slot 7h that comprises a left-handed thread 7e, on which is threaded a knurled nut 14 displaceable forward and rearward. The sliding sleeve 13 is operationally connected with the knurled nut 14 by way of the hook 13a in a way to make the nut 14 freely rotatable. It is thus possible to displace the grip chuck forward and backward by rotating the knurled nut 14.

Inside the grip chuck 10 is disposed a longitudinally displaceable ejector 15. This ejector 15 essentially consists of a relatively thin pin having its front portion 15a guided inside the front end of the grip chuck holder 11a, and its rear end provided with a thickened portion 15b guided inside the bore of the milling cutter holder 7. This thickened portion 15b is fixedly connected with an ejector sleeve 17 by means of a throughgoing pin 16, the rear end 17a of the ejector sleeve 17 being displaceably covered by the coring cutter holder 7, whereas its front end 17b is covered by the knurled nut 14. Slots 7f provided in the coring cutter holder 7, and of which only one is shown in the drawing, are effective to limit the displacement of the ejector 15 in both directions.

A spring ring 18 which when opened is able to escape into the U-shaped annular groove 17c of the sleeve 17 constituted, together with a slot 7g provided in the coring cutter holder 7, a springing detent for the ejector sleeve. The sleeve and with it the ejector are thus prevented from becoming unintentionally displaced in forward direction.

The method of functioning readily follows from the foregoing.

The excision of a bone biopsy is started by first boring a tubular hole into the bone by means of a tubular coring cutter. As soon as the hole has reached its desired or needed depth, the motor drive is stopped by releasing the depressor knob 2 that actuates the switch and, at the same time, the knurled nut 14 is fixedly held by means of the second hand. Since the drive shaft 6 and the milling cutter holder 7 connected therewith will continue to turn for a little while, the knurled nut 14 will get screwed forwardly, with the result that the sliding sleeve 13, too, and the grip chuck 10 rigidly connected with it by way of the pin 12 and the grip chuck holder 11, will be displaced in forward direction. As a result of the inward thickening of the coring cutter end 9a, the grip chuck 10 will be closed and will fixedly hold the milled-out bone stud. Thus, when pulling out the milling cutter from the hole, the bone stud will be broken off and taken along, whereby the breaking off may take place as a result of the fact, that the coring cutter and the grip chuck, while the latter is in closed position, will keep rotating for a little while. Subsequently, the knurled nut is turned back by hand, thus pulling back the grip chuck and releasing the milled-out bone stud. Displacing the ejector sleeve 17 forwardly will cause the ejector 15 too to be displaced in forward direction, thus pushing out the stud.

Sterilization may be accomplished by unscrewing the device from the thread 6a of the drive shaft 6. Since this screwed-on device comprises only metal parts, it may be readily sterilized. Also, it may be cleaned relatively easily in the following manner. Subsequent to loosening the socket head cap screw 8 the coring cutter 9 may be removed from the milling cutter holder, thus releasing the grip chuck 10, so that the milling cutter and the grip chuck may be cleaned independently of each other. If a drive comprising an electrical motor that may be sterilized is used, then the entire power tool may be sterilized in an autoclave without previous disassembly.

While there are shown and described present preferred embodiments of the invention, it is to be distinctly understood, that the invention is not limited thereto but may be otherwise variously embodied and practiced within the scope of the appended claims.

What is claimed is:

1. Device for excising a bone or cartilage biopsy shaped as a stud, the device comprising an axially extending tubular coring cutter adapted to be connected to a drive shaft of a boring tool in a manner to transmit torque to the coring cutter, wherein an axially extending grip chuck axially displaceable relative to the coring cutter and serving as extractor is disposed inside the coring cutter, and an axially displaceable ejector is provided inside the grip chuck.

2. Device as claimed by claim 1, wherein the tubular coring cutter is loosenably held inside a coring cutter holder adapted to be rigidly connected with said drive shaft, said coring cutter holder being provided with an external thread on which is disposed a knurled nut adapted to be screwed forward and backward and being operatively connected with a sliding sleeve, the sliding sleeve being rigidly connected by way of a grip chuck holder with the grip chuck, by at least one radial pin displaceable in the axial direction of said coring holder between two end positions with an axially extending slot of the coring cutter holder.

3. Device as claimed in 2, wherein the grip chuck is fitted inside a bore of the tubular coring cutter, also, a wall of the tubular coring cutter is thickened radially inwardly in a free end region of the coring cutter, and wherein an inside diameter of the coring cutter as measured at its free end is equal to the inside diameter of the grip chuck in its retracted position, and during forward displacement free ends of grip chuck ribs in said grip chuck are made to get closer to each other, thus effecting a decrease in the size of a grip chuck opening adjacent the free end of said coring cutter.

4. Device as claimed in claim 2, wherein said tubular coring cutter cutting in a clockwise direction has the external thread provided on the coring cutter holder formed as a left-handed thread.

5. Device as claimed in claim 2, wherein the ejector is formed as an axially displaceable pin fixedly connected with an ejector sleeve by means of a radially extending pin displaceable within an axially extending slot of the coring cutter holder between two end positions spaced apart in the axial direction, the ejector sleeve having an end facing away from the coring cutter fitted on the coring cutter holder and being held fast in a retracted position within a springing detent.

* * * * *